United States Patent
Noske et al.

[11] 3,976,889
[45] Aug. 24, 1976

[54] X-RAY DIAGNOSTIC APPARATUS

[75] Inventors: Erich Noske, Erlangen; Ulrich Grassme, Nurnberg, both of Germany

[73] Assignee: Siemens Aktiengesellschaft, Erlangen, Germany

[22] Filed: Aug. 23, 1974

[21] Appl. No.: 500,111

[30] Foreign Application Priority Data
Sept. 19, 1973  Germany............................ 2347178

[52] U.S. Cl................................ 250/510; 250/402
[51] Int. Cl.² ........................................ G21K 3/50
[58] Field of Search ........... 250/415, 510, 491, 492, 250/402, 409

[56] References Cited
UNITED STATES PATENTS

| | | |
|---|---|---|
| 2,542,022 | 2/1951 | Friedman............................ 250/510 |
| 2,901,631 | 8/1959 | Hansen et al........................ 250/510 |
| 3,164,723 | 1/1965 | Boldingh............................. 250/415 |
| 3,631,527 | 12/1971 | Splain ................................ 250/409 |
| 3,746,862 | 7/1973 | Lombardo et al. ................ 250/409 |
| 3,862,426 | 1/1975 | Thomas .............................. 250/402 |

*Primary Examiner*—Alfred E. Smith
*Assistant Examiner*—P. C. Anderson
*Attorney, Agent, or Firm*—Haseltine, Lake & Waters

[57] ABSTRACT

An X-ray diagnostic apparatus for X-ray exposures, having preset X-ray tube voltage and current values, and a preset exposure time and, more particularly, to an apparatus of this type which includes a plurality of filters in conformance with an exposure program for the X-radiation adapted to be selectively employed in coordination with a particular exposure object.

6 Claims, 4 Drawing Figures

X-RAY DIAGNOSTIC APPARATUS

FIELD OF THE INVENTION

The present invention relates to an X-ray diagnostic apparatus for X-ray exposures, having preset X-ray tube voltage and current values, and a preset exposure time and, more particularly, to an apparatus of this type which includes a plurality of filters in conformance with an exposure program for the X-radiation adapted to be selectively employed in coordination with a particular exposure object.

DISCUSSION OF THE PRIOR ART

An X-ray diagnostic apparatus of this type, for example, it utilized in the formation of dental exposures. In order to provide coordination with the particular object which is to be filmed, it is known to employ a timing switch or an mAs-relay. It is also known that operating keys may be used for the control of the mAs-relay, which are associated with the individual teeth. Prior to the completion of an exposure the key associated with a particular tooth which is to be X-rayed, must be depressed for effecting selection of the corresponding mAs-product. The determination of the mAs-product is carried out by means of an electronic switching installation which is influenced by the operating key. The electronic components are located in a panel which is associated with a single housing-like constructed X-ray diagnostic apparatus, and which also supports the exposure triggering mechanism.

SUMMARY OF THE INVENTION

Accordingly, it is an object of the present invention to provide an X-ray diagnostic apparatus of the above-described type having a construction which, in comparison with the state of the technology, is essentially greatly simplified and considerably less expensive. In particular, there is thus obviated the need for a special control panel for the setting of the exposure data.

The foregoing object is inventively attained through the provision of an X-ray diagnostic apparatus for X-ray exposures having fixedly set values for the X-ray tube voltage and current, and the exposure time and wherein for a particular exposure program a plurality of filters are provided for the X-radiation in coordination with a particular exposure object and in which a support arrangement is provided for the filters, through the intermediary of which a filter may be selectively interposed into the path of the X-radiation.

Thus, pursuant to the inventive object, the coordination of the filter and the particular object which is to be exposed is carried out by interposing the particularly required filter into the path of the X-radiation. The arrangement which supports the filters may be directly positioned on the housing which contains the X-ray tubes. The inventive X-ray diagnostic apparatus is particularly adapted to the completion of dental exposures, in which the X-ray tubes and the high-voltage generator are located in an oil-filled housing, and the support arrangement for the filters is located intermediate an X-ray outlet aperture and a tube which focuses the X-radiation.

BRIEF DESCRIPTION OF THE DRAWINGS

Further advantages and details of the invention may now be ascertained from the following description of an exemplary embodiment thereof, taken in conjunction with the accompanying drawings, in which.

DETAILED DESCRIPTION

Figure 1:
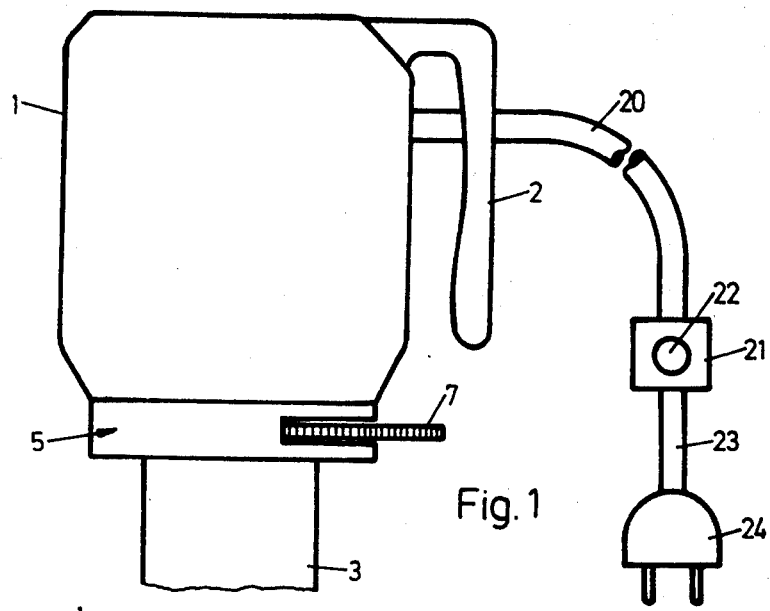
FIG. 1 shows an elevational view of an X-ray diagnostic apparatus constructed in accordance with the present invention.

The X-ray diagnostic apparatus illustrated in the drawings comprises a single or unitary enclosure apparatus utilized for dental exposures. The apparatus according to FIG. 1 includes, in a known manner, a housing 1 filled with oil and which contains therein an X-ray tube, as well as an associated high-voltage generator. The housing 1 is adjustable into the exposure position by means of a suitable handgrip 2. The X-radiation exits through a tube 3 which focuses the X-rays.

The X-ray diagnostic apparatus is connected, by means of a cable 20, with a timing switch 21, the latter of which possesses a push button 22. A cable 23 leads from the timing switch 21 to an electrical supply plug 24.

Figure 2:
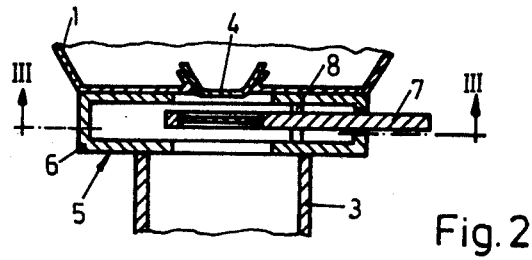
FIG. 2 is a sectional view taken through the support arrangement for the filter-containing portion of the X-ray diagnostic apparatus according to FIG. 1.

From FIG. 2 it may be ascertained that the housing 1 includes an X-ray outlet aperture 4 for the X-radiation, and a filter arrangement 5 which is positioned intermediate the tube 3 and the X-radiation outlet aperture 4, the filter arrangement possessing a ray-impervious housing 6 within which there is supported a disc 7. The disc is rotatably supported proximate the X-ray outlet aperture 4 about an axis 8 which extends eccentrically to the main X-ray beam 16 (FIG. 3).

Figure 3:
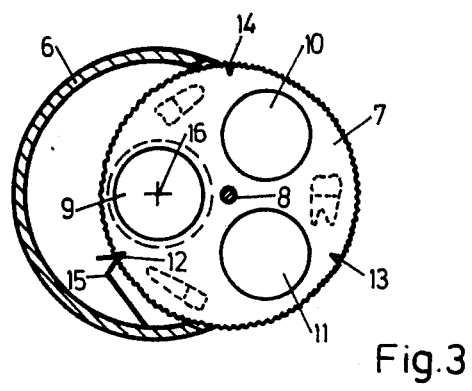
FIG. 3 is a sectional view taken along line III—III in FIG. 2.

The disc 7, in accordance with FIG. 3, includes three apertures, within which there are located three filters 9 through 11 for the X-radiation, and which have their center points located on a circle extending concentrically about axis 8. The radius of this circle is equal to the distance between the central or main X-ray beam 16 and the rotational axis 8. By effecting rotation of disc 7, which is serrated about its rim, one of the filters 9 through 11 may, respectively, be moved centrally below the X-ray outlet aperture 4. For this purpose, disc 3 includes three locking notches or recesses 12 through 17 spaced about its periphery into which a locking spring 15 is adapted to engagingly snap when respectively one of the filters 9 through 11 is centrally located below the X-ray outlet aperture 4.

The filters 9 through 11 may, for example, consist of aluminum discs having varied thicknesses. The X-ray diagnostic apparatus possesses a fixedly set X-ray tube voltage and X-ray tube current of, for example, respectively, 60 kV and 7 mA, and a fixedly set exposure time of, for example, 1 second. The coordination with or matching to the particular exposure object, meaning, the particular tooth which is to be X-rayed, is carried out by positioning of the filter which is associated with that tooth below the X-ray outlet aperture 4.

In practice, it is adequate to have coordination of the X-radiation to the types of teeth which are known as "molars, bicuspids and incisors". The upper surface of disc 7 has corresponding symbols designated thereon. Since the disc 7 has its rim project somewhat outwardly of housing 6 for enabling manual manipulation thereof, the particular tooth symbol on the projecting portion is visible, from above which is associated with the filter positioned below the X-ray outlet aperture 4. It has been indicated that two filters, which consist of aluminum discs having thicknesses of, respectively, 0.5 mm and 1 mm, as well as one aperture in the disc without a filter are suitable for coordinating with the particular exposure object in conformance with the three above-mentioned types of teeth.

In the inventive X-ray diagnostic apparatus there is completely eliminated the need for a control panel for carrying out the setting of the exposure data. The coordination with the particular exposure object is effected by means of disc 7, which is directly located on the single-housing apparatus. The inventive object has, in comparision with the state of the technology, in addition to a simpler construction also the essential advantage that, notwithstanding a constant X-ray voltage, the X-ray penetration is changed by the filters in conformance with the exposure object, which meets the requirement of X-raying thin objects with a soft X-radiation in order to obtain a good contrast. In the inventive disclosure, a filter having a relatively strong absorption value for X-radiation must be employed for the X-raying of thin objects. Within the scope of the invention, the primary circuit which essentially incorporates the timing switch, may be constructed as a unitary entity with the single-housing generator, since no operative adjustments need be carried out in the primary circuit.

Figure 4:
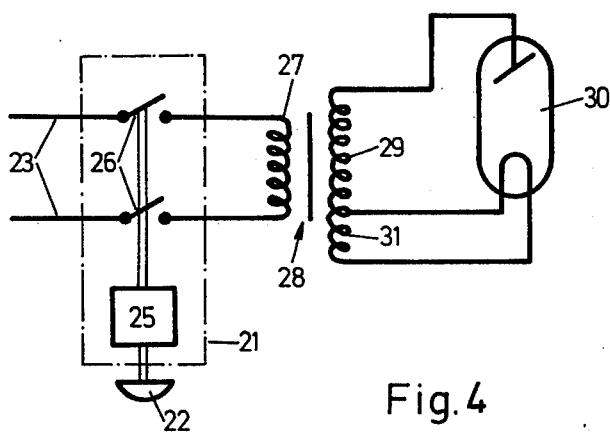
FIG. 4 is a schematic circuit diagram for an X-ray diagnostic apparatus according to the invention.

From the circuit diagram illustrated in FIG. 4 it may be ascertained that the timing switch 21 includes a timer 25, the latter of which actuates contacts 26 connecting the power supply conduit 23 with the primary winding 27 of a high-voltage transformer 28. The timer 25 has a push button 22 associated therewith. The secondary winding of the high-voltage transformer 28 is divided into two portions. The winding portion 29 transmits the anode voltage for the X-ray tubes 30, and the winding portion 31 transmits the filament voltage.

From FIG. 4 it may be ascertained that the anode voltage, as well as the filament voltage, and consequently the X-ray tube current, are each constant. A constant time is programmed into the timer 25. Upon depression of the push button 22 for commencing an X-ray exposure, the switches 26 are closed and the programmed time begins to run. After completion of this time, the timer 25 opens the switches 26 and terminates the exposure. From FIG. 4 it may thus be ascertained that the X-ray diagnostic apparatus is provided with only a single value for, respectively, the exposure time, high voltage for the X-ray tube, and X-ray tube current.

While there has been shown what is considred to be the preferred embodiment of the invention, it will be obvious that modificaions may be made which come within the scope of the disclosure of the specification.

What is claimed is:

1. In an X-ray diagnostic apparatus for the preparation of dental X-ray exposures including means for fixedly setting values for the X-ray tube voltage and current, the improvement comprising: means for fixedly setting the exposure time; a plurality of filters for the X-radiation each coordinated with a particular exposure object in conformance with an exposure program in which the fixed values for said X-ray tube voltage, X-ray tube current and exposure time cannot be varied by a user of said diagnostic apparatus; and support means for said filters, said support means being adapted to selectively position a preselected one of said filters at any one time in the path of said X-radiation in conformance with a predetermined selected exposure object.

2. An apparatus as claimed in claim 1, said apparatus including an X-ray outlet aperture facilitating through passage of a central X-ray beam, said filter support means comprising a disc located proximate to said X-ray outlet aperture and being rotatable about an axis eccentric relative to said central X-ray beam, said filters being circumferentially spaced about said disc so as to have the centerpoints thereof define a circle concentric to the rotational axis of said disc, the radius of said circle corresponding to the distance between said central X-ray beam and said rotational axis.

3. An apparatus as claimed in claim 2, comprising a housing encompassing said filters and said filter support means, said disc having a rim portion thereof projecting outwardly of said housing adapted to facilitate manual rotational movement of said filters.

4. An apparatus as claimed in claim 3, comprising indicia indicative of the exposure object associated with a respective of said filters being provided on said portion of the disc projecting outwardly of said housing.

5. An apparatus as claimed in claim 1, said apparatus comprising a single-enclosure collectively housing the components of said X-ray diagnostic apparatus adapted for dental X-ray exposures.

6. An apparatus as claimed in claim 5, comprising primary switching circuit means for actuation of said apparatus, said single-enclosure including a generator, said generator and said circuit being constructed as a unitary entity.

* * * * *